United States Patent [19]

Rizzuto et al.

[11] 4,154,655

[45] May 15, 1979

[54] METHOD FOR THE PRODUCTION OF CEPHALOSPORIN C

[75] Inventors: Anthony B. Rizzuto, Piscataway, N.J.; Richard D. Skole, Elmhurst, N.Y.; Henry H. Newman, Bronx, N.Y.; Jacqueline N. Hogu, Brooklyn, N.Y.; Vincent A. Toscano, Lawrenceville, N.J.

[73] Assignee: Amstar Corporation, New York, N.Y.

[21] Appl. No.: 736,489

[22] Filed: Oct. 28, 1976

Related U.S. Application Data

[62] Division of Ser. No. 617,369, Sep. 29, 1975, Pat. No. 4,003,791, which is a division of Ser. No. 485,730, Jul. 3, 1974, abandoned.

[51] Int. Cl.$^2$ ............................................. C12D 9/04
[52] U.S. Cl. ................................................. 195/36 C
[58] Field of Search ..................................... 195/36 C

[56] References Cited

U.S. PATENT DOCUMENTS

| | | | |
|---|---|---|---|
| 3,082,155 | 3/1963 | Kelly et al. | 195/36 C |
| 3,816,257 | 6/1974 | Yamano et al. | 195/36 C |
| 3,825,473 | 7/1974 | Gargiuolo | 195/36 C |

*Primary Examiner*—Alvin E. Tanenholtz
*Attorney, Agent, or Firm*—Cooper, Dunham, Clark, Griffin & Moran

[57] ABSTRACT

It has been discovered that a material consisting essentially of a high-ash-containing sucrose syrup, said sucrose syrup containing about 70–90% by weight solids and analyzing on a solids basis about 40–85% by weight sucrose, about 8–35% by weight invert, about 3–25% by weight ash, the remaining percent being other organic components, such as pectins, products formed by the action of heat and amino acids and alkali upon reducing sugars and up to about 10% by weight polysaccharides, is useful as a component in a medium for the growth of microorganisms. The syrup is usefully employed in a minor amount, e.g., in the range about 4–8% weight/volume in the growth medium, the syrup being added as a carbohydrate or carbon source for the growth of the microorganism. The above-described syrup is particularly useful as a component of a growth medium for the production of penicillin from a penicillin-producing microorganism and for the production of cephalosporin C by a cephalosporin C-producing microorganism.

2 Claims, 1 Drawing Figure

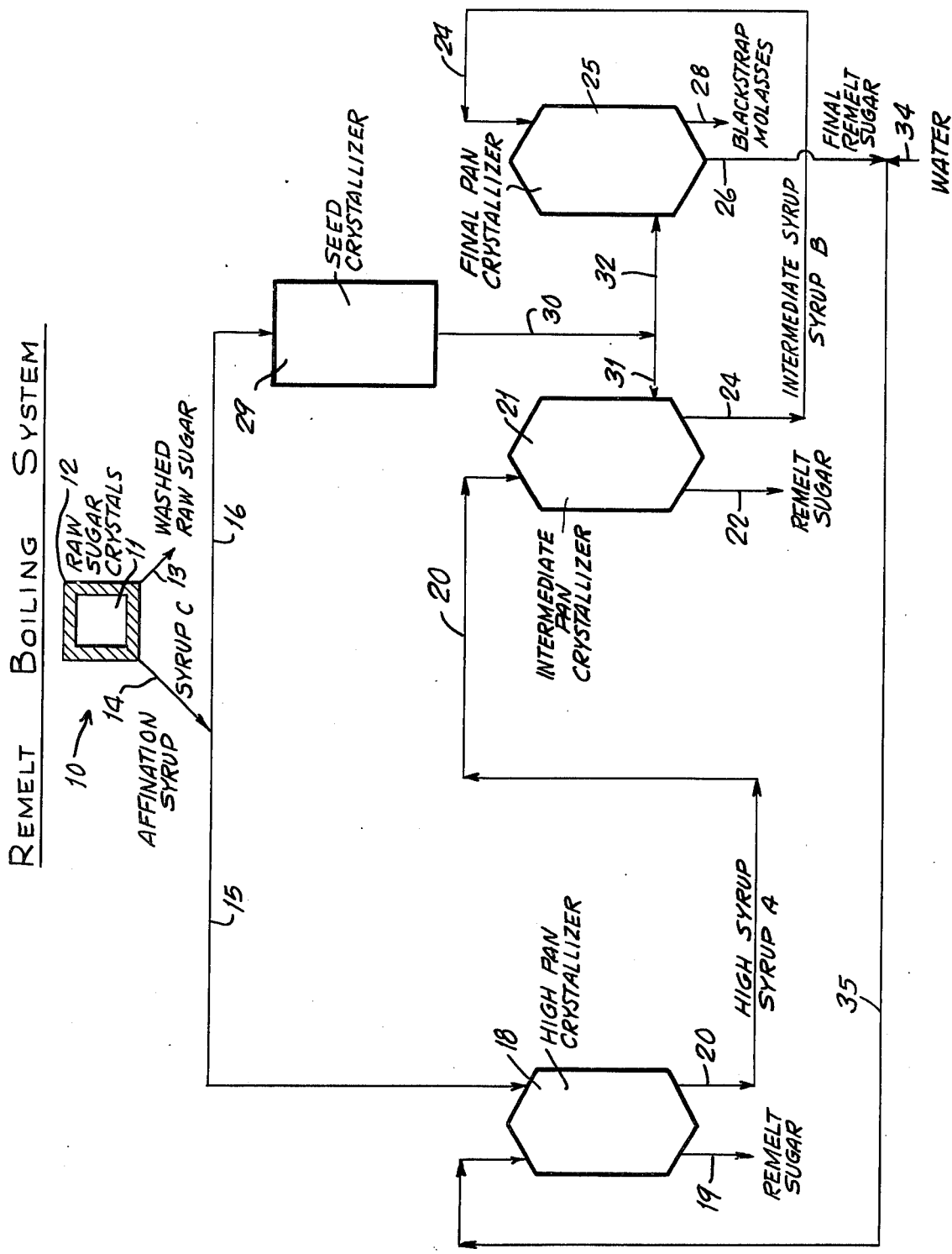

METHOD FOR THE PRODUCTION OF CEPHALOSPORIN C

This is a division of application Ser. No. 617,369 filed Sep. 29, 1975 of Anthony Benny Rizzuto et al now U.S. Pat. No. 4,003,791 which in turn is a division of parent application Ser. No. 485,730 filed July 3, 1974, now abandoned.

This invention relates to the growth of microorganisms. In one embodiment, this invention relates to a material useful as a component in a growth medium for the growth of microorganisms. In another embodiment, this invention is useful for the preparation of a growth medium for the growth of microorganisms therein. In accordance with still another embodiment, this invention is directed to an improved method and growth medium for the production of penicillin and cephalosporin C and other useful materials.

In the growth of microorganisms, one of the components of the growth medium is a carbohydrate or carbon source. A variety of carbohydrates have been so employed. For example, a variety of carbohydrates are useful as a component of a growth medium for the growth of the penicillin-producing microorganism, *Penicillum chrysogenun*, the microorganism usually employed for the production of penicillin. Carbohydrates which have been employed as a carbohydrate source to provide energy and carbon for the growth of a penicillin-producing microorganism include starch, dextrins, sucrose and glucose.

A growth medium for the production of penicillin by the growth of the microorganism *Penicillum chrysogenum* therein would include in its make-up corn steep liquor solids, lactose and glucose and the salts sodium nitrate, calcium carbonate and phenylacetic acid or a derivative thereof. Because of the high cost of glucose and lactose as the carbohydrate component of the growth medium, penicillin producers have long sought to employ less costly carbohydrate sources but which would produce large or equivalent penicillin yields and at a lower unit manufacturing cost. To this end, it has been proposed to employ hydrol molasses, a product of the corn industry, as a carbohydrate source or substrate in connection with penicillin production. A typical growth medium composition for the production of penicillin by the growth of *Penicillium chrysogenum* therein has the composition on a weight/volume relationship: 3% corn steep liquor, 2% lactose, 0.5% glucose, 0.2% $NaNO_3$, 0.5% $CaCO_3$ and 0.05% of phenylacetic acid or a derivative thereof, the growth medium having a pH of about 6.0 and capable of being sterilized by autoclaving at a temperature of about 121° C. for about 15 minutes.

Accordingly, it is an object of this invention to provide a new and useful carbohydrate source for use in growth media for the cultivation of microorganisms therein.

It is another object of this invention to provide an improved process, and growth medium useful therein, for the growth of microorganisms, particularly those microorganisms which are a source of or which during growth produce a valuable and/or useful product, such as penicillin, cephalosporin C, polysaccharides, gibberellic acid, riboflavin, nucleotides, citric acid and other useful materials, such as yeast.

How these and other objects of this invention are achieved will become apparent in the light of the accompanying disclosure and drawing wherein there is illustrated a flow chart showing the production of the special high-ash-containing syrups employed in the practices of this invention. In at least one embodiment of the practice of this invention, at least one of the foregoing objects will be achieved.

It has been discovered that a high-ash-containing sucrose syrup is especially useful as a carbohydrate source in a growth medium for the cultivation of microorganisms therein. The high-ash-containing sucrose syrup useful in accordance with this invention has a total solids content in the range about 70-90% by weight and analyzes on a solids basis about 40-85% by weight sucrose, about 8-35% by weight invert, about 3-25% by weight ash, the remaining percent being other organic components, such as up to about 10% by weight polysaccharides, and pectins and the products formed by the action of heat and amino acids and alkali upon reducing sugars. The ash of the high-ash-containing sucrose syrup in accordance with this invention analyzes about 2-50% by weight calcium, e.g., about 8-46% by weight calcium, about 0.5-8% by weight magnesium, e.g., about 1-7% by weight magnesium, about 0.1-3.5% by weight sodium, e.g., 0.2-3% by weight sodium, about 3-35% by weight potassium, e.g., about 10-34% by weight potassium, about 0.05-0.6% by weight iron, e.g., about 0.1-0.5% iron, about 0.001-1.0% by weight copper, e.g., about 0.1-0.09% by weight copper, about 0.1-0.6% other heavy metals, about 3-55% by weight sulfate and about 0.5-15% by weight phosphate, e.g., about 2-14% by weight phosphate.

Typical high-ash-containing sucrose syrups useful as providing carbohydrate sources in the preparation of growth media for microorganisms in accordance with this invention would contain about 70-74% by weight solids, averaging about 72% by weight solids, or 78-81% solids, averaging about 79.5% by weight solids, or 79-87% solids, averaging about 81.0% by weight solids.

Set forth in accompanying Table I are the analyses of high-ash-containing syrups useful in accordance with the practices of this invention:

TABLE I

| | Syrup A* | Syrup B* | Syrup C* |
|---|---|---|---|
| Sucrose | 53-66% | 41-59% | 73-84% |
| Invert | 8-22% | 13-30% | 5-12% |
| Ash | 8-13% | 8-20% | 3-8% |
| Organic Undetermined | 10-24% | 14-25% | 6-14% |
| Inorganic - As a Percent of Ash | | | |
| Calcium | 8-41% | 8-46% | 4-40% |
| Magnesium | 2-6% | 2-7% | 1-7% |
| Sodium | 0.8-2% | 0.7-3% | 0.2-3% |
| Potassium | 11-34% | 10-32% | 10-35% |
| Iron | 0.1-0.5% | 0.1-0.5% | 0.1-2% |
| Copper | 0.01-0.09% | 0.02-0.08% | 0.02-0.5% |
| Heavy Metals | 0.1-0.3% | 0.2-0.6% | 0.07-0.3% |
| Sulfate | 4-53% | 11-44% | 9-49% |
| Phosphate | 2-14% | 2-6% | 0.8-4% |

*All percentages reported on a total solids basis.

These high-ash sucrose syrups exhibit high density, about 11.6 pounds per gallon, are liquid at room temperature, are biologically stable but exhibit high microbial growth potential when diluted, exhibit low impurity partition coefficient towards immiscible organic solvents, possess color and trubidity-causing components which have a high affinity towards adsorbents therefor, exhibit high buffer (pH) properties, exhibit high filterability at low densities and, when diluted, possess a high degree of thermal stability, i.e., withstand without deterioration or undesirable reaction temperatures necessary for sterilization, and exhibit a high solubility in water.

Especially useful as a high-ash-containing syrup in accordance with this invention is a syrup having the composition set forth in accompanying Table II.

TABLE II

| | |
|---|---|
| Total Solids (true) | 74.0% ± 2.0% |
| Total Sugars | 70% Min. (Dry Basis) |
| Sucrose (Polarization/RDS) | 50% Min. (Dry Basis) |
| Invert | 20% Min. (Dry Basis) |
| Ash + Undetermined Organics | 30% Max. (Dry Basis) |
| pH | 5.5 ± 1.0 |
| Density | 11.64 ± 0.15 lb/gal |

Typical Analysis of Ash as Percent of Dry Solids

| | |
|---|---|
| K | 3.44% |
| Ca | 2.39% |
| $SO_4$ | 1.43% |
| Mg | 0.45% |
| $PO_4$ | 0.30% |
| Si | 0.20% |
| Na | 0.12% |
| Fe | 0.06% |
| Al | 0.04% |
| Rb | 0.01% |
| Mn | 0.004% |
| Cu | 0.003% |
| Sr | 0.003% |
| Ba | 0.001% |
| Ti | 0.001% |
| Li | Trace |
| V | Trace |
| Pb | Trace |
| Mo | Trace |
| B | Trace |

Undetermined organics include: polysaccharides, pectins, and products formed by the action of heat, amino acids and alkali upon reducing sugars.

The syrups found to be useful as a component of growth media for the production of microorganisms, particularly to provide a carbon source, have not heretofore been commercially available. These syrups are produced in the refining of raw cane sugar for the production of a finished sugar product. The syrups in accordance with this invention are produced when raw sugar, which consists of relatively pure sucrose crystals surrounded by a film of relatively impure syrup, is refined so as to effect separation of the impure syrup from the sucrose crystals. The separated syrup is accumulated and processed through a recovery system referred to in the cane sugar refining trade as the remelt boiling process. Syrup A mentioned hereinabove is a syrup resulting from the first crystallization step in the recovery system and Syrup B is a syrup resulting from the second crystallization step in the recovery system. A so-called affination, such as Syrup C, identified hereinabove, a basic feed material to the recovery system, is also useful. As mentioned hereinabove, the high-ash-containing syrups, such as Syrups A, B and C hereinabove, have not heretofore been available in commerce but were produced as intermediate process streams in a sugar refining operation for the ultimate production of pure sucrose crystals or sugar. Heretofore, these syrups were not considered to have any separate commercial value or utility.

The preparation of the syrups useful in the practices of this invention is illustrated in the accompanying drawing illustrative of the so-called remelt boiling process in the refining of cane sugar. As illustrated in the drawing, a mass of raw sugar crystals, generally indicated by reference numeral 10, made up of sucrose crystals 11 coated with a film 12 of a liquid, molasses-like material containing a minor amount of sucrose dissolved therein together with other sugars, such as invert, and dissolved salts, is washed with a substantially saturated sucrose solution to wash away or dissolve film 12 from sucrose crystals 11. Desirably, the substantially saturated sucrose solution employed to wash mass 10 of raw sugar is derived from a previous washing step. The resulting wash liquor, so-called affination syrup, equivalent to Syrup C identified hereinabove as a syrup useful in the practices of this invention, is separated from the resulting washed raw sugar and supplied via line 14 to lines 15 and 16. The resulting washed raw sugar is passed via line 13 for further processing.

Affination syrup flowing in line 15 is introduced into high pan crystallizer 18 wherein water is evaporated therefrom and the resulting sucrose crystals separated via line 19. The mother liquor, identified as high syrup, a syrup equivalent to Syrup A identified hereinabove as being useful in the practices of this invention is separated from the crystallizer 18 via line 20 and introduced into intermediate pan crystallizer 21 wherein it is subjected to additional crystallization for sugar (sucrose) recovery, the resulting crystallized sugar being removed from crystallizer 20 via line 22.

The mother liquor from intermediate crystallizer 21 is withdrawn via line 24. This mother liquor, a so-called intermediate syrup, is equivalent to the above-described Syrup B for use in the practices of this invention. The intermediate syrup removed from intermediate crystallizer 21 via line 24 is introduced into final pan crystallizer 25 wherein it is subjected to a crystallization operation for the recovery of sugar (sucrose) therefrom, the resulting crystallized sugar being recovered from final crystallizer 25 via line 26 and the mother liquor, so-called black-strap molasses, is recovered from crystallizer 25 via line 28.

In the operation of intermediate crystallizer 21 and final crystallizer 25, seed crystals derived from affination syrup 14 supplied via line 16 to seed crystallizer 29 are supplied thereto via line 30 and lines 31 and 32, respectively. Also, as indicated, the crystallized sugar recovered from final crystallizer 25 via line 26 is dissolved with water supplied via line 34 and the resulting solution or suspension passed via line 35 to high pan crystallizer 18 for ultimate recovery of the sugar via line 19.

Tests were carried out to demonstrate the utility of the high-ash-containing sucrose syrups of this invention. In these tests, the evaluation being carried out on the basis of penicillin production, the syrups of this invention, such as Syrups A, B and C hereinabove, along with a commercial syrup from the corn processing industry, known as hydrol molasses, were substituted for the lactose and glucose in a base growth medium having the composition on a weight/volume basis of 3% corn steep liquor, 2% lactose, 0.5% glucose, 0.2% $NaNO_3$, 0.5% $CaCO_3$ and 0.05% of phenylacetic acid, the final pH of the medium being 6.0 with sterilization of the medium being accomplished by autoclaving at 121° C. for 15 minutes. The test syrups, for example, Syrups A and B identified hereinabove, and the hydrol molasses tested were employed in the growth medium in the amount 4% weight/volume.

In the test evaluations, *Penicillium chrysogenum* ATCC 11710 was inoculated into the shaker flask with the medium containing the various syrups to be evaluated. The pH was noted daily during fermentation until a decline in antibiotic production was noted. The fermentations were carried out in shaker flasks utilizing a New Brunswick Scientific Co., Inc. gyrotory incubator shaker at 28.5° C. The flasks were shaken or moved in a 1 inch circle. The test syrups, Syrups A and B, were obtained from different lots of raw sugar for each run. The penicillin produced within the test media made up of the various carbohydrate substrates tested was determined microbiologically by the assay disc method utilizing *Sarcina lutea* ATCC 9341 as the penicillin sensitive microorganism. Zones of inhibition were read on a Fischer-Lilly Zone Reader. The results of the tests are set forth in accompanying Tables III and IV.

TABLE III

Penicillin Production Employing Various Substrates as a Carbohydrate Source

| Substrates | Penicillin Production, Relative % | Day of Highest Production | pH at Day of Highest Production |
|---|---|---|---|
| Run I | | | |
| Base Medium | 100 | 4 | 7.8 |
| Syrup A | 84 | 4 | 8.5 |
| Syrup B | 104 | 4 | 8.4 |
| Hydrol Molasses | 72 | 4 | 8.2 |
| Run II | | | |
| Base Medium | 100 | 3 | 7.7 |
| Syrup A | 121 | 3 | 8.0 |
| Syrup B | 103 | 3 | 8.2 |
| Hydrol Molasses | 30 | 3 | 7.6 |
| Run III | | | |
| Base Medium | 100 | 4 | 7.9 |
| Syrup A | 221 | 3 | 8.6 |
| Syrup B | 187 | 3 | 8.6 |
| Hydrol Molasses | 98 | 3 | 8.5 |
| Run IV | | | |
| Base Medium | 100 | 4 | 7.6 |
| Syrup A | 93 | 3 | 8.2 |
| Syrup B | 99 | 4 | 8.7 |
| Hydrol Molasses | 49 | 3 | 8.4 |

TABLE IV

| Substrates | Relative % Average Penicillin Produced |
|---|---|
| Base Medium | 100 |
| Syrup A | 130 |
| Syrup B | 123 |
| Hydrol Molasses | 62 |

The thermal stability of the syrups of this invention, particularly Syrup A and Syrup B, and the color passthrough or transference of these syrups and hydrol molasses during penicillin extraction were also investigated. In a commercial fermentation operation for antibiotic, e.g., penicillin, production it is necessary to sterilize the growth medium. Due to the large volume of growth medium necessary to be sterilized in a commercial operation, there is a slow comeup time resulting in an extended period wherein the growth medium is subjected to high temperature. In an effort to ascertain the thermal stability of the syrups of this invention, such as Syrups A and B, the growth media containing these syrups were subjected to an extended period of autoclaving (1 hour at 121° C.) as well as to the standard period of autoclaving (15 minutes at 121° C.). The results indicated a high degree of thermal stability for the syrups of this invention and the yields of penicillin produced from media containing the syrups of this invention when subjected to an extended period of high temperature, were not reduced, see accompanying Table V.

TABLE V

Comparison of Penicillin Production Employing Selected Cane Sugar Substrates as a Carbohydrate Source Subjected to High Temperature (121° C.) for 15 Minutes Vs. 1 Hr.

| Substrate | 15 Minutes | 1 Hour |
|---|---|---|
| Syrup A | 100% | 128% |
| Syryp B | 100% | 104% |

An important consideration in ascertaining whether or not a given substrate is acceptable for use in a commercial fermentation medium for antibiotic production is the degree of resistance of color transference during penicillin extraction. Some of the commonly used solvents for penicillin extraction include amylacetate and butylacetate. In an effort to compare the color transference during penicillin extraction from growth media incorporating therein Syrup A and Syrup B with that of media containing hydrol molasses, the extraction of penicillin after 4 days of fermentation was made with these two solvents. The results of these tests are set forth in accompanying Tables VI and VII.

TABLE VI

Color Passed Into Amylacetate During Penicillin Extraction

| | Carbohydrate Substrate | | |
|---|---|---|---|
| | Syrup A | Syrup B | Hydrol Molasses |
| Color of Medium After 4 Days Fermentation | 2,960* | 3,788* | 3,038* |
| Color of Amylacetate Extract | 150* | 142* | 123* |
| % Color Extracted into Amylacetate | 5.1 | 3.8 | 4.1 |

*In mau (milli-absorbence units)

TABLE VII

Color Passed into Butylacetate During Penicillin Extraction

| | Carbohydrate Substrate | | |
|---|---|---|---|
| | Syrup A | Syrup B | Hydrol Molasses |
| Color of Medium After 4 Days Fermentation | 2,925* | 3,946* | 2,023* |
| Color of Butylacetate Extract | 234* | 292* | 264* |
| % Color Extracted into Butylacetate | 8.0 | 7.4 | 13.0 |

*In mau (milli-absorbence units)

There appeared to be no appreciable difference in the degree of color extracted by the solvents from growth media containing Syrup A, Syrup B and that of growth media containing hydrol molasses as the carbohydrate source. The results set forth hereinabove indicate that the high-ash sucrose syrups in accordance with this invention having an ash content in the range from about 3–25%, such as in the range 8–20%, by weight gave a significantly high average total antibiotic yield as compared with the conventional commercially employed hydrol molasses which contains only about 2.25% by weight ash.

Additional tests as described in connection with the data presented in Table III were also carried out employing Syrup C as the carbohydrate (carbon) source in the fermentation medium for the production of penicillin. The results of these tests are set forth in Table VIII.

TABLE VIII

Penicillin Production Employing Various Substrates as a Carbohydrate Source

| Substrates | Penicillin Production, Relative % | Day of Highest Production | pH at Day of Highest Production | % of Test Substrate Substituted in Base Medium |
|---|---|---|---|---|
| Run I | | | | |
| Base Medium (Contrl) | 100 | 4 | 7.8 | — |
| Syrup C | 97 | 4 | 8.5 | 4 |
| Hydrol Molasses | 72 | 4 | 8.2 | 4 |
| Run II | | | | |
| Base Medium (Control) | 100 | 4 | 7.8 | — |
| Syrup C | 118 | 3 | 8.4 | 4 |
| Hydrol Molasses | 64 | 3 | 7.7 | 4 |
| Run III | | | | |
| Base Medium (Control) | 100 | 3 | 7.7 | — |
| Syrup C | 124 | 3 | 8.3 | 4 |
| Hydral Molasses | 30 | 3 | 7.6 | 4 |
| Run IV | | | | |
| Base Medium (Control) | 100 | 3 | 7.7 | — |
| Syrup C | 100 | 3 | 8.1 | 8 |
| Hydrol Molasses | 98 | 3 | 8.7 | 4 |
| Run V | | | | |
| Base Medium (Control) | 100 | 3 | 8.0 | — |
| Syrup C | 210 | 5 | 8.1 | 8 |
| Hydrol Molasses | 99 | 3 | 8.6 | 4 |

Additionally, the thermal stability of Syrup C and the usefulness of Syrup C after having been subjected to a high temperature for penicillin production was investigated. The results of these tests are set forth in accompanying Table IX:

TABLE IX

Comparison of Penicillin Production With Syrup Substrate Subjected to High Temperature (121° C.) for 15 Minutes Vs. 1 Hour

| Substrate | 15 Minutes | 1 Hour |
|---|---|---|
| Syrup C | 100% | 119% |

Likewise, the color passthrough of Syrup C was compared with hydrol molasses in a penicillin extraction and the results of these tests are set forth in accompanying Table X:

TABLE X

Color Passed into Amylacetate During Penicillin Extraction

| | Carbohydrate Substrate | |
|---|---|---|
| | Syrup C | Hydrol Molasses |
| Color of Medium After 4 Days Fermentaton | 2,381* | 3,038* |
| Color of Amylacetate Extract | 124* | 123* |
| % Color Extracted into Amylacetate | 5.2 | 4.1 |

*In mau (milli-absorbence units)

The results of these tests show that Syrup C, like Syrups A and B and the blends thereof, all being high-ash content sucrose syrups having the compositions described hereinabove, are useful as substrates for carbohydrate or carbon sources in growth media for the fermentation production of antibiotics, such as penicillin and the like, and are generally useful as carbohydrate or carbon sources for the growth of microorganisms. ;p Syrups A, B and C hereinabove, in addition to being useful for the production of penicillin, are also useful for the production of other antibiotics, such as cephalosporin C, streptomycin, terramycin and other antimicrobial and/or antifungal antibiotics.

Additional tests were carried out to demonstrate the practices of this invention, and the benefits obtainable therefrom, with respect to the preparation of cephalosporin C. The results of these tests indicated that 64% more cephalosporin C was produced in a medium containing a high-ash sucrose syrup in accordance with this invention, such as Syrup B, as compared with cephalosporin C produced in another growth medium wherein the carbohydrate source, instead of being a high-ash sucrose syrup in accordance with this invention, was a beet molasses, such as Steffenized beet molasses. Steffenized beet molasses analyzes about 70% by weight solids, about 53% by weight sucrose, about 2% by weight reducing sugars, about 15% by weight ash (sulfated) and about 30% by weight undetermined organics. The base medium employed in these tests, a modification of the medium reportedly used for cephalosporin C, analyzes 3% weight/volume beef extract, 0.5% weight/volume corn steep liquor, 0.15% weight-/volume calcium carbonate, 0.5% weight/volume DL methionine and 2% weight/volume methyl oleate, the medium having a pH of 7.0. When Steffenized beet molasses, a conventional component of the base medium, is present, it is present in the amount of 4% weight/volume. When the high-ash sucrose containing syrups of this invention is employed, it is substitutedfor the Steffenized beet molasses in an equivalent amount, i.e., 4% weight/volume.

The greater productivity of a growth medium containing the high-ash sucrose syrups of this invention in place of the commercially conventionally employed Steffenized beet molasses as the carbon source is indicated in the accompanying Table XI presenting data based on 16 tests.

TABLE XI

Comparative Cephalosporin C Producton Beet Molasses Vs. High-Ash Syrup Fermentation Substrate as the Carbon Source

| Substrate | Average Cephalosporin Production, Relative % |
|---|---|
| Base Medium (Containing Beet Molasses as the Carbon Source) | 100 |
| Base Medium (Syrup B Substituted for the Beet Molasses) | 164 |

Further tests indicative of the superiority of the high-ash sucrose syrups as a carbon source for the production of cephalosporin C are reported in the accompanying Tables XII, XIII, XIV and XV.

TABLE XII

Comparative Cephalosporin C Production Beet Molasses Vs. Syrup B in

TABLE XII-continued
Fermentation Substrate as the Carbon Source

| Substrate | Cephalosporin C Production, Relative % | Day of Highest Production | pH at Day of Highest Production |
|---|---|---|---|
| Base Medium (Containing Beet Molasses) | 100 | 3 | 6.9 |
| Syrup B | 163 | 4 | 7.8 |

Syrup Chemical Analysis

| | Syrup B |
|---|---|
| % Solids | 77.95 |
| Sucrose | 52.34 (Pol.) |
| Reducing Sugars | 15.39 |
| Ash (Sulfated) | 15.41 |
| Orgaic Undetermined | 16.86 |

TABLE XIII
Comparative Cephalosporin C Production Beet Molasses Vs. Syrup B in Fermentation Substrate as the Carbon Source

| Substrate | Cephalosporin C Production, Relative % | Day of Highest Production | pH at Day of Highest Production |
|---|---|---|---|
| Base Medium (Containing Beet Molasses) | 100 | 4 | 7.3 |
| Syrup B | 158 | 3 | 7.5 |

Syrup Chemical Analysis

| | Syrup B |
|---|---|
| % Solids | 84.05 |
| Sucrose | 55.66 (Clerget) |
| Reducing Sugars | 17.80 |
| Ash (Thermal) | 8.56 |
| Organic Undetermined | 17.98 |

TABLE XIV
Comparative Cephalosporin C Production Beet Molasses vs. Syrup B in Fermentation Substrate as the Carbon Source

| Substrate | Cephalosporin C Production, Relative % | Day of Highest Production | pH at Day of Highest Production |
|---|---|---|---|
| Base Medium (Containing Beet Molasses) | 100 | 3 | 7.2 |
| Syrup B | 259 | 3 | 7.9 |

Syrup Chemical Analysis

| | Syrup B |
|---|---|
| % Solids | 80.85 |
| Sucrose | 54.90 (Pol.) |
| Reducing Sugars | 13.20 |
| Ash (Sulfated) | 11.90 |
| Organic Undetermined | 20.00 |

TABLE XV
Comparative Cephalosporin C Production Beet Molasses Vs. Syrup B in Fermentation Substrate as the Carbon Source

| Substrate | Cephalosporin C Production, Relative % | Day of Highest Production | pH at Day of Highest Production |
|---|---|---|---|
| Base Medium (Containing Beet Molasses) | 100 | 3 | 7.4 |
| Syrup B | 172 | 3 | 7.4 |

Syrup Chemical Analysis

| | Syrup B |
|---|---|
| % Solids | 75.33 |
| Sucrose | 53.17 (Clerget) |
| Reducing Sugars | 24.74 |
| Ash (Thermal) | 6.89 |
| Organic Undetermined | 15.20 |

TABLE XVI
Comparative Cephalosporin C Production Beet Molasses Vs. Syrup B in Fermentation Substrate as the Carbon Source

| Substrate | Cephalosporin C Production, Relative % | Day of Highest Production | pH at Day of Highest Production |
|---|---|---|---|
| Base Medium (Containing Beet Molasses) | 100 | 3 | 7.3 |
| Syrup B | 146 | 3 | 7.2 |

Syrup Chemical Analysis

| | Syrup B |
|---|---|
| % Solids | 83.26 |
| Sucrose | 51.60 (Pol.) |
| Reducing Sugars | 18.20 |
| Ash (Sulfated) | 12.90 |
| Organic Undetermined | 17.30 |

TABLE XVII
Comparative Cephalosporin C Production Beet Molasses Vs. Syrup B in Fermentation Substrate as the Carbon Source

| Substrate | Cephalosporin C Production, Relative % | Day of Highest Production | pH at Day of Highest Production |
|---|---|---|---|
| Base Medium (Containing Beet Molasses) | 100 | 3 | 7.7 |
| Hydrol Molasses | 107 | 3 | 7.2 |
| Syrup B | 161 | 3 | 7.7 |
| Syrup B | 148 | 3 | 7.4 |
| Syrup B | 136 | 3 | 7.3 |

Chemical Analysis

| Tests | Hydrol Molasses |
|---|---|
| % Solids | 86.09 |
| Sucrose | — |
| Reducing Sugars | 80.68 |
| Ash (Sulfated) | 2.27 |
| Organic Undetermined | 17.05 |

TABLE XVIII
Comparative Cephalosporin C Production Beet Molasses and Other Substrates Vs. Syrup B in Fermentation Substrate as the Carbon Source

| Substrate | Cephalosporin C Production, Relative % | Day of Highest Production | pH at Day of Highest Production |
|---|---|---|---|
| Base Medium (Containing Steffenized Beet Molasses) | 100 | 4 | 7.3 |
| Sucrose Syrup (Substantially no Ash) | 78 | 3 | 6.4 |
| Sucrose Syrup | | | |

TABLE XVIII-continued

| | | | |
|---|---|---|---|
| + 500 ppm of a Mixture of Natural Amino Acids (Stamino) | 100 | 3 | 6.6 |
| Unsteffenized Beet Molasses | 95 | 3 | 7.8 |
| Syrup B | 157 | 3 | 7.5 |

Chemical Analysis of Test Substrates

| Tests | Sucrose Syrup | Sucrose Syrup + 500 ppm of a Mixture of Natural Amino Acids | Unsteffenized Beet Molasses |
|---|---|---|---|
| % Solids | 67.53 | 68.95 | 79.72 |
| Sucrose | 99.44 (Pol.) | 99.72 (Pol.) | 59.73 (Clerget) |
| Reducing Sugars | .25 | 0.07 | 2.08 |
| Ash (Sulfated) | .10 | 0.03 | 17.11 |
| Organic Undetermined | .21 | 0.11 | 21.08 |

Though the test results reported herein and illustrating the superiority of the practices of this invention are particularly directed to the fermentative production of antibiotics, such as penicillin and cephalosporin C, the advantages of the practices of this invention are also realizeable, as indicated hereinabove, with respect to the production of other antibiotic materials and other chemicals and other materials, such as citric acid, gibberellic acid, yeast and the like.

As will be apparent to those skilled in the art in the light of the accompanying disclosure, many modifications, substitutions and alterations are possible in the practices of this invention without departing from the spirit or scope thereof.

We claim:

1. A method for the production of cephalosporin C which comprises growing a cephalosporin C-producing microorganism in a culture medium in the presence of an added amount of a high-ash containing sucrose syrup, said amount being in the range about 4–8% weight/volume in said medium, said sucrose syrup analyzing on a solids basis, about 40–85% by weight sucrose, about 8–35% by weight invert, about 3–25% by weight ash, the remaining percent being other organic components.

2. A method for producing cephalosporin C which comprises growing a cephalosporin C-producing microorganism in a culture medium in the presence of an added amount of a high-ash containing sucrose syrup, said amount being in the range about 4–8% by weight/volume in said medium, said sucrose syrup analyzing on a solids basis about 40–85% by weight sucrose, about 8–35% by weight invert, about 3–25% by weight ash, the remaining percent being other organic components, said syrup having a total solids content in the range 70–90% by weight of the syrup and the ash content of said syrup analyzing about 2–50% by weight calcium, about 0.5–8% by weight magnesium, about 0.1–3.5% by weight sodium, about 3–35% by weight potassium, about 0.05–0.6% by weight iron, about 0.001–1.0% by weight copper, about 3–55% by weight sulfate and about 0.5–15% by weight phosphate.

* * * * *